United States Patent [19]

Zenitz

[11] 4,008,276

[45] Feb. 15, 1977

[54] PHENYL-LOWER-ALKYLAMINES

[75] Inventor: Bernard L. Zenitz, Colonie, N.Y.

[73] Assignee: Sterling Drug Inc., New York, N.Y.

[22] Filed: Dec. 22, 1975

[21] Appl. No.: 642,758

Related U.S. Application Data

[62] Division of Ser. No. 542,552, Jan. 20, 1975, Pat. No. 3,965,105.

[52] U.S. Cl. .................. 260/570.5 P; 260/348 R; 260/501.1; 260/501.11; 260/501.2; 260/501.21; 260/558 R; 260/592; 260/599; 424/316; 424/330
[51] Int. Cl.² ......................................... C07C 91/28
[58] Field of Search .................. 260/570.5 P, 501.1

[56] References Cited
UNITED STATES PATENTS 3,126,381   3/1964   Lanzis et al. ............... 260/570.5 X

OTHER PUBLICATIONS

Stavrovskaya et al., "Chemical Abstracts", vol. 50, p. 1765 (1956).
Damiens, "Chemical Abstracts", vol. 47, pp. 2695–2696 (1953).

Primary Examiner—Robert V. Hines
Attorney, Agent, or Firm—William G. Webb; B. Woodrow Wyatt

[57]  ABSTRACT

Phenyl-lower-alkylamines having anti-inflammatory activity are prepared either by reductive alkylation of an amine with a phenyl-lower-alkanaldehyde; by condensation of a phenyl-lower-alkanaldehyde with a secondary amine, conversion of the resulting phenyl-vinylamine to the corresponding iminium salt, and reduction of the latter with an alkali metal borohydride; or by reaction of a phenyl-lower-alkanoyl halide with an amine and reduction of the resulting amide with a reagent effective to reduce an amide to an amine.

2 Claims, No Drawings

PHENYL-LOWER-ALKYLAMINES

RELATED APPLICATIONS

This is a division of my prior application Ser. No. 542,552, filed Jan. 20, 1975, now U.S. Pat. No. 3,965,105, patented June 22, 1976.

BACKGROUND OF THE INVENTION a. Field of the Invention

This invention relates to phenyl-lower-alkylamines useful as anti-inflammatory agents.

b. Description of the Prior Art

A very large class of organic compounds of widely diverse structural types are known to be useful as anti-inflammatory agents, but many of such anti-inflammatory agents are acidic, for example α-(4-isobutylphenyl)propionic acid, known generically as ibuprofen (French Patent 1,545,270, delivre Sept. 30, 1968). Such acidic agents are often irritating, and in some cases are ulcerogenic, to the gastric mucosa when administered orally. There is thus a great need for anti-inflammatory agents, for example compounds having a basic amine function, which might be expected to be nonirritating to the gastric mucosa. Although the chemical literature describes numerous types of amine-substituted compounds asserted to have anti-inflammatory activity [see for example U.S. Pat. Nos. 3,770,748, patented Nov. 6, 1973 and 3,803,127, patented Apr. 9, 1974 (N-phenylpolymethyleneimines); U.S. Pat. Nos. 3,772,311, patented Nov. 13, 1973 and 3,773,772, patented Nov. 20, 1973 (polymethyleneimino-lower-alkanoylpyrazoles); U.S. Pat. No. 3,773,944, patented Nov. 20, 1973 (1-[3-aminopropyl]phthalans); U.S. Pat. No. 3,801,594, patented Apr. 2, 1974 (3-amino-lower-alkylindoles); and U.S. Pat. No. 3,810,985, patented May 14, 1974 (4-anilino-1,3,5-triazines)], no such basic compounds are presently known to be commercially available, and none are presently known to be under advanced investigation by pharmacologists for possible commercial development. The search for an effective, non-acidic anti-inflammatory agent for commercial development therefore continues.

SUMMARY OF THE INVENTION

In one of its composition of matter aspects, the invention relates to certain phenyl-lower-alkylamines:

which are useful as anti-inflammatory agents.

In a second composition of matter aspect, the invention relates to certain phenyl-lower-alkanoylamines:

which are useful as intermediates for the preparation of the final products.

In one of its process aspects, the invention relates to a process for preparing the phenyl-lower-alkylamines which comprises the reductive alkylation of an amine, H-N=B, with a phenyl-lower-alkanal:

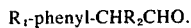

In a second process aspect, the invention relates to a process for preparing the phenyl-lower-alkylamines which comprises reducing, with an alkali metal borohydride, a phenyl-lower-alkyliminium salt:

In a third process aspect, the invention relates to a process for preparing the phenyl-lower-alkylamines which comprises reducing a phenyl-lower-alkanoylamine:

with reagents effective to reduce amides to amines, for example an alkali metal aluminum hydride, a trialkylaluminum or a dialkylaluminum hydride.

DETAILED DESCRIPTION INCLUSIVE OF THE PREFERRED EMBODIMENTS

More specifically, the invention relates to phenyl-lower-alkylamines, which are useful as anti-inflammatory agents, having the formula:

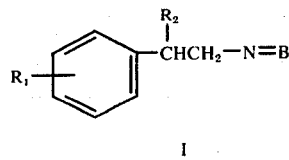

where $R_1$ represents hydrogen, lower-alkyl, lower-alkenyl or halogen; $R_2$ represents hydrogen or lower-alkyl; and N=B represents one of the groups

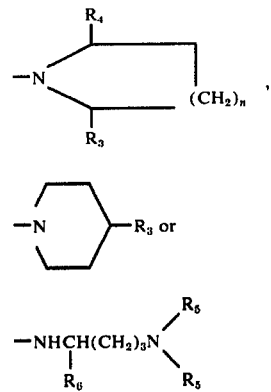

where $R_3$ represents lower-alkyl, cyclohexyl or cyclohexyl-lower-alkyl; $R_4$ and $R_6$ represent hydrogen or lower-alkyl; $R_5$ represents lower-alkyl; and n represents one of the integers 1, 2 and 3.

Particularly preferred compounds within the ambit of the invention as described above are those of the above formula I where $R_1$ represents hydrogen, lower-alkyl or halogen; $R_2$ represents lower-alkyl; and N=B represents one of the groups

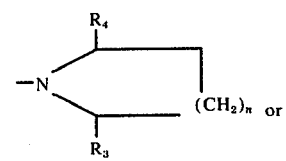

-continued

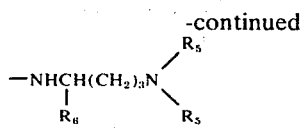

where $R_3$ represents lower-alkyl or cyclohexyl-lower-alkyl; $R_4$ represents hydrogen or lower-alkyl; $R_5$ and $R_6$ represent lower-alkyl; and n represents one of the integers 1 and 2.

As used herein, the term lower-alkyl means saturated, monovalent aliphatic radicals, including branched chain radicals, of from one to four carbon atoms, for example methyl, ethyl, propyl, isopropyl, butyl, sec.-butyl and isobutyl.

As used herein, the term lower-alkenyl means monovalent radicals containing from two to five carbon atoms and possessing a single double bond, for example vinyl, 1-(2-propenyl), 1-(2-methyl-2-propenyl), 1-(3-methyl-2-butenyl) and 1-(2-methyl-2-butenyl).

The compounds of formula I are prepared by reductive alkylation of an appropriate amine, H-N=B, with an appropriate phenyl-lower-alkanal of formula II. The method is carried out by reducing a mixture of the amine and the aldehyde with hydrogen in the presence of a catalyst and is represented by the reaction:

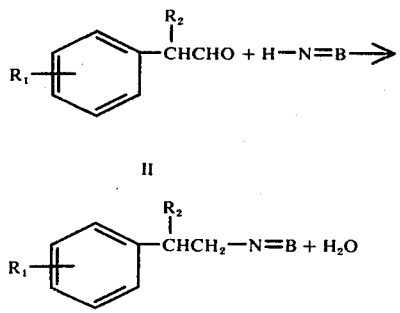

where $R_1$, $R_2$ and N=B have the meanings given above. The reaction is preferably carried out in a lower-alkanol solvent at hydrogen pressures in the range from 40 to 80 p.s.i. Preferred catalysts are palladium-on-charcoal or Raney nickel.

Alternatively, the compounds of formula I where N=B is one of the groups

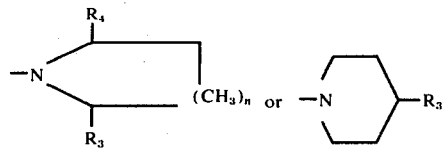

can be prepared by reaction of an appropriate phenyl-lower-alkanal of formula II with a secondary amine having the formula

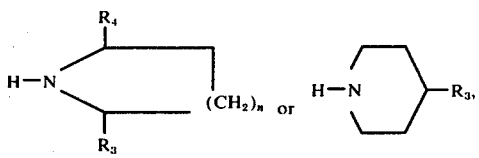

conversion of the resulting phenylvinylamine of formula III to the iminium salt having the formula IV by reaction of the former with mineral acid, and reduction of the iminium salt with an alkali metal borohydride. The method is represented by the reaction sequence:

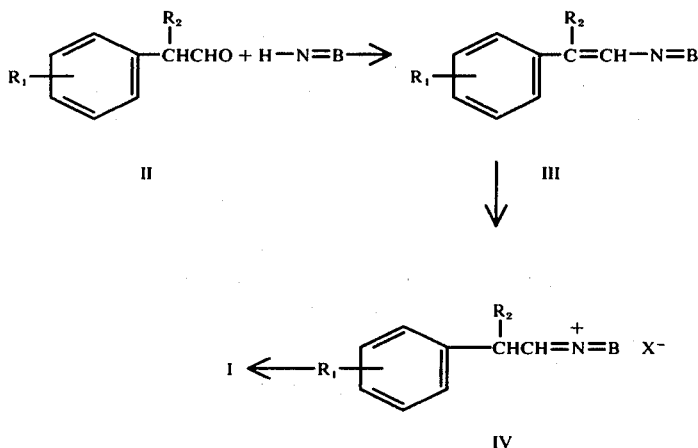

where $R_1$, $R_2$ and N=B have the meanings given above, an $X^-$ represents an anion of a strong mineral acid. The condensation of the aldehyde and the amine is preferably carried out in a water immiscible solvent, for example benzene, toluene or xylene at the reflux temperature thereof and under a water separator which is used to collect the water as it is produced in the reaction. The reduction of the iminium salt with an alkali metal borohydride is carried out in an inert organic solvent, for example a lower-alkanol or dimethylformamide. The above described method is particularly advantageous for the preparation of the compounds of formula I where $R_1$ is halogen or lower-alkenyl which cannot be prepared by methods involving catalytic reduction, since such method would lead to compounds wherein a halogen atom is subjected to hydrogenolysis and a lower-alkenyl group is reduced to the corresponding lower-alkyl group.

Another method for preparing the compounds of formula I comprises reacting an appropriate phenyl-lower-alkanoyl halide of formula VI (prepared by reaction of the corresponding acid of formula V with a thionyl halide) with an appropriate amine, H-N=B, and reduction of the resulting phenyl-lower-alkanoylamine of formula VII with a reagent effective to reduce amides to amines, for example in alkali metal aluminum hydride, a trialkylaluminum or a dialkylaluminum hydride. The method is represented by the following reaction sequence:

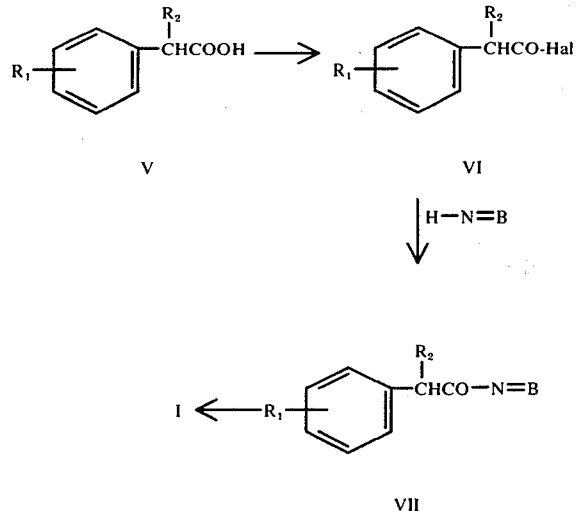

where $R_1$, $R_2$ and N=B have the meanings given above, and Hal represents halogen.

The preparation of the amides of formula VII is essentially a "one-pot" reaction involving reaction of the acid of formula V with a thionyl halide in a non-protolytic organic solvent, for example benzene, toluene or xylene, at the reflux temperature thereof and addition of the acid halide, without isolation or further purification, either in the same solvent or in a different non-protolytic solvent, for example diethyl ether, dioxane or tetrahydrofuran, to a solution of the amine, H-N=B, in a non-protolytic solvent. The latter reaction is preferably carried out at ambient temperature and in the presence either of a molar excess of the amine or in the presence of an acid-acceptor, for example pyridine, a tri-lower-alkylamine, dimethylaniline or an alkali metal carbonate.

The amines, H-N=B, where -N=B is the group

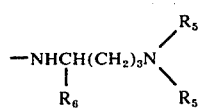

are known compounds.

The amines were N=B is the group

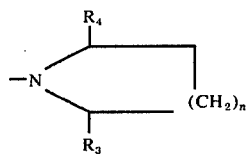

where $n$ is 2 are also known, having been generally described in U.S. Pat. No. 3,238,215. As described therein, they are prepared by catalytic reduction over platinum oxide of appropriate 2-substituted (or 2,6-disubstituted) pyridines, which are commercially available.

The amines where N=B is the group

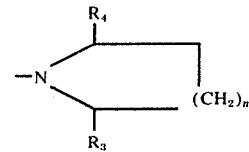

where $n$ is the integer 1 are prepared by refluxing a mixture of an appropriate alkanedione, ammonium acetate and glacial acetic acid, and catalytic reduction over platinum oxide of the resulting 2-$R_3$-5-$R_4$-pyrrole according to the reaction sequence:

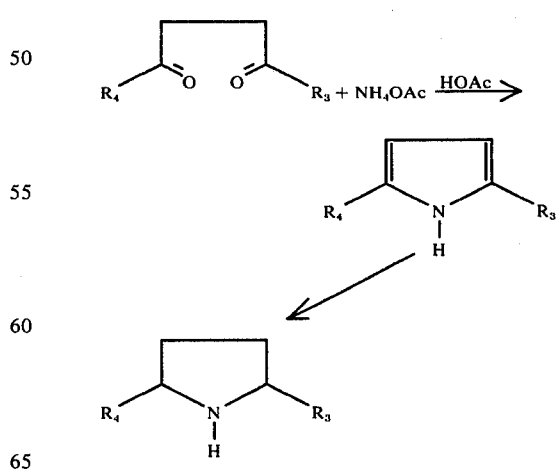

where $R_3$ and $R_4$ have the meanings given above.

Alternatively, the amines where -N=B is the group

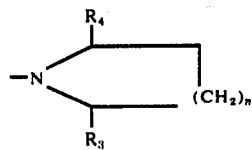

where *n* is 1 are prepared by reaction of a Grignard reagent, $R_3MgHal$ with a 4-$R_4$-4-halobutyronitrile, $R_4$-CH(HAL)-(CH$_2$)$_2$-CN; direct cyclization of the resulting 1-amino-1-$R_3$-4-$R_4$-4-halo-1-butene; and catalytic reduction of the resulting 2-$R_3$-5-$R_4$-4,5-dihydropyrrole as indicated by the reaction sequence:

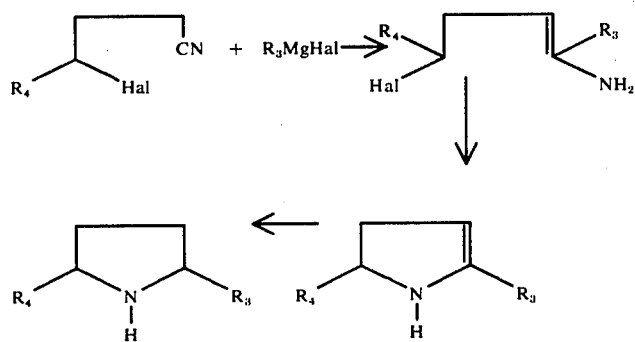

where $R_3$, $R_4$ and Hal have the meanings given above.

The amines where -N=B is the group:

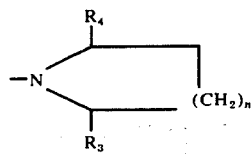

where *n* is the integer 3, $R_4$ is hydrogen and $R_3$ has the meanings given above are prepared by Beckmann rearrangement of an appropriate $R_3$ substituted-cyclohexanone oxime and reduction, with lithium aluminum hydride, of the resulting lactam according to the reaction:

The amines where -N=B is the group:

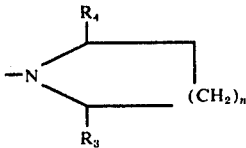

are advantageously prepared, like the amines where -N=B is the group:

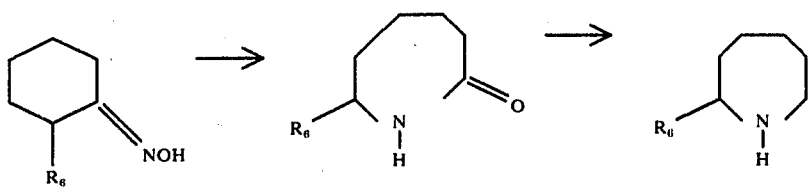

where *n* is 2, by catalytic reduction over platinum oxide of the corresponding 4-$R_3$-pyridine.

The phenyl-lower-alkanals of formula II and the phenyl-lower-alkanoic acids of formula V where $R_2$ is hydrogen are known compounds. The aldehydes and acids where $R_2$ is lower-alkyl are prepared by Friedel-Crafts reaction of an appropriate $R_1$-substituted-benzene with a lower-alkanoic acid anhydride and conversion of the resulting lower-alkanophenone to a phenyl-lower-alkanal via the Darzens glycidic ester condensation by reaction of the lower-alkanophenone with a lower-alkyl haloacetate in the presence of an alkali metal alkoxide and saponification and decarboxylation of the resulting glycidic ester. Oxidation of the aldehyde with silver nitrate affords the corresponding acid. The method is represented by the following reaction sequence:

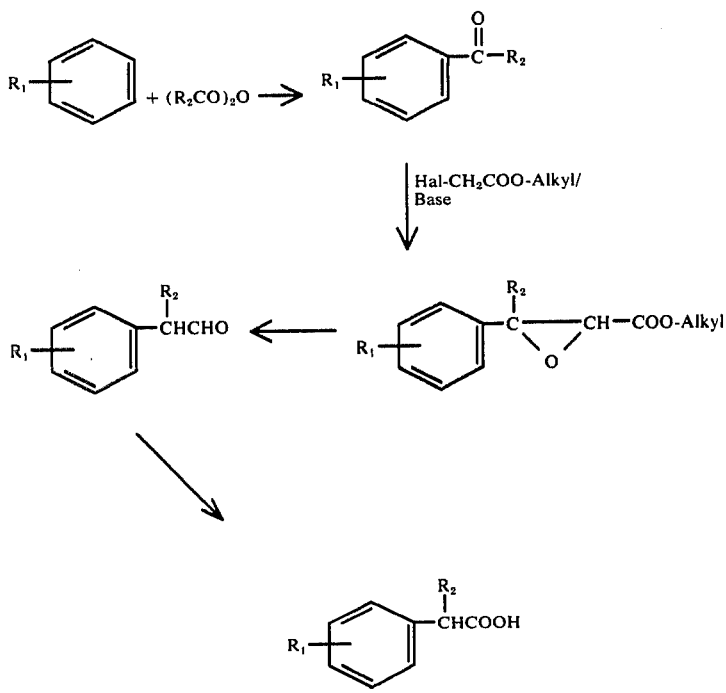

where $R_1$, $R_2$ and Hal have the meanings given above, and Alkyl represents a lower-alkyl group.

The novel compounds of the instant invention are the compounds of formula I and the acid-addition salts thereof. The compounds of formula I in free base form are converted to the acid-addition salt form by interaction of the base with an acid. In like manner, the free base can be regenerated from the acid-addition salt form in the conventional manner, that is by treating the salts with cold, weak aqueous bases, for example alkali metal carbonates and alkali metal bicarbonates. The bases thus regenerated can then be interacted with the same or a different acid to give back the same or a different acid-addition salt. Thus the novel bases and all of their acid-addition salts are readily interconvertible.

It will thus be appreciated that formula I not only represents the structural configuration of the bases of formula I but is also representative of the structural entity which is common to all of the compounds of formula I, whether in the form of the free base or in the form of the acid-addition salts of the base. It has been found that by virtue of this common structural entity, the bases and their acid-addition salts have inherent pharmacological activity of a type to be more fully described hereinbelow. This inherent pharmacological activity can be enjoyed in useful form for pharmaceutical purposes by employing the free bases themselves or the acid-addition salts formed from pharmaceutically-acceptable acids, that is, acids whose anions are innocuous to the animal organism in effective doses of the salts so that beneficial properties inherent in the common structural entity represented by the free bases is not vitiated by side effects ascribable to the anions.

In utilizing this pharmacological activity of the salts of the invention, it is preferred, of course, to use pharmaceutically-acceptable salts. Although water-insolubility, high toxicity, or lack of crystalline character may make some particular salt species unsuitable or less desirable for use as such in a given pharmaceutical application, the water-insoluble or toxic salts can be converted to the corresponding pharmaceutically-acceptable bases by decomposition of the salt with aqueous base as explained above, or alternatively, they can be converted to any desired pharmaceutically-acceptable acid-addition salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically-acceptable free bases by reaction of the salts with aqueous bases, or alternatively can be converted to a pharmaceutically-acceptable acid-addition salt by, for example, ion-exchange procedures.

It will be appreciated from the foregoing that all of the acid-addition salts of the new bases are useful and valuable compounds, regardless of considerations of solubility, toxicity, physical form, and the like, and are accordingly within the purview of the instant invention.

The novel feature of the compounds of the invention, then, resides in the concept of the bases and cationic forms of the new phenyl-lower-alkylamines and not in any particular acid moiety or acid anion associated with the salt forms of the compounds; rather, the acid moieties or anions which can be associated in the salt forms are in themselves neither novel nor critical and therefore can be any acid anion or acid-like substance capable of salt formation with the bases. In fact, in aqueous solutions, the base form or water-soluble acid-addition salt form of the compounds of the invention both possess a common protonated cation or ammonium ion.

Thus, appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isethionic acid, benzenesulfonic acid, p-toluene-sulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophoshoric acid, arsenic acid, picric acid, picrolonic acid, barbituric acid, boron trifluoride, and the like.

The acid-addition salts are prepared by reacting the free base and acid in an organic solvent and isolating the salt directly or by concentration of the solution.

Due to the presence of at least one and as many as three asymmetric centers in the compounds of the invention, i.e., the carbon atom of the group -N=B to which the group $R_3$ is attached, the carbon atom adjacent the secondary nitrogen atom of the group -N=B when $R_6$ is lower-alkyl in the group

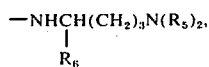

and the carbon atoms to which the groups $R_2$ and $R_4$ are attached when other than hydrogen, the compounds of the invention can exist in stereochemically isomeric forms, which are all considered to be within the purview of the invention. If desired, the isolation or the production of a particular stereochemical form can be accomplished by application of general principles known in the art.

In standard pharmacological test procedures, the compounds of formula I have been found to possess anti-inflammatory activity and are useful as anti-inflammatory agents. Anti-inflammatory activity was determined using (1) the inhibition of carrageenin-induced foot edema test essentially described by Van Arman et al., J. Pharmacol, Exptl. Therap. 150, 328 (1965) as modified by Winter et al., Proc. Soc. Exp. Biol. and Med. 111, 544 (1962) and (2) a modification of the inhibition of adjuvant-induced arthritis test described by Pierson, J. Chronic Diseases 16, 863 (1963) and Glenn et al., Am. J. Vet. Res. 26, 1180 (1965).

The compounds of the invention can be prepared for use by incorporating them in unit dosage form as tablets or capsules for oral administration either alone or in combination with suitable adjuvants such as calcium carbonate, starch, lactose, talc, magnesium stearate, gum acacia, and the like. Still further, the compounds can be formulated for oral administration in aqueous alcohol, glycol or oil solutions or oil-water emulsions in the same manner as conventional medicinal substances are prepared.

The molecular structures of the compounds of the invention were assigned on the basis of study of their infrared, ultraviolet, and NMR spectra, and confirmed by the correspondence between calculated and found values for elementary analyses for the elements.

The following examples will further illustrate the invention without, however, limiting it thereto. All melting points are uncorrected.

PREPARATION OF INTERMEDIATES

Preparation 1

In three separate runs, 33.8 g. (0.20 mole) portions of 2-benzylpyridine, each in a solution of about 225 ml. of ethanol and 22 ml. of concentrated hydrochloric acid, were reduced over 4.0 g. portions of platinum oxide catalyst under about 54 p.s.i. of hydrogen at a temperature of about 55°–61° C. When reduction was complete in each case, the catalyst was removed by filtration, washed with small portions of ethanol, and the combined filtrates evaporated to a volume of about 80 ml. and diluted to approximately 500 ml. with boiling acetone. The solid which precipitated was collected, washed with acetone and dried giving a combined yield of 124.8 g. of 2-cyclohexylmethylpiperidine hydrochloride, m.p. 211°–213° C. The free base was regenerated from the hydrochloride by neutralization of an aqueous solution of the latter with potassium carbonate, extraction of the oily base into benzene, evaporation of the benzene solution to dryness, and distillation of the residual oil in vacuo at 55°–59° C./0.27 mm. There was thus obtained 89.4 g. of 2-cyclohexylmethylpiperidine.

Preparation 2

A mixture of 15.52 g. (0.10 mole) of 2-phenylpyridine, 15 ml. of concentrated hydrochloric acid and 2.0 g. of platinum oxide in 185 ml. of ethanol in a pressure bottle was heated and shaken in a Parr hydrogenater under 55 p.s.i. of hydrogen at a temperature around 60° C. When reduction was complete in about eight hours, the catalyst was removed by filtration and the filtrate concentrated to about 50 ml. and diluted with 200 ml. of acetone. The solid which separated was collected and dried to give 14.54 g. of 2-cyclohexylpiperidine hydrochloride, m.p. 251°–253° C.

Preparation 3

A mixture of 9.1 g. (0.05 mole) of 2-stilbazole (Shaw et al., J. Chem. Soc. 1933, 77-79) and 1.0 g. of platinum oxide in a solution of 240 ml. of ethanol and 10 ml. of concentrated hydrochloric acid in a pressure bottle was heated and shaken on a Parr hydrogenator under about 55 p.s.i. of hydrogen at a temperature of about 60° C. When reduction was complete in about eight hours, the catalyst was removed by filtration, the filtrate concentrated to a volume of about 50 ml. and diluted with about 200 ml. of acetone. The solid which separated was collected and dried to give 9.6 g. of 2-(2-cyclohexylethyl)-piperidine hydrochloride, m.p. 155°–156° C.

Preparation 4

A solution of 78.1 g. (0.84 mole) of 4-methylpyridine and 89.0 g. (0.84 mole) of benzaldehyde in 103 g. of acetic anhydride was heated with stirring under reflux for 24 hours. The mixture was then concentrated to a thick oil in vacuo and the residue dissolved in hot ethanol. The solid which separated was collected and recrystallized from ethanol to give 57.9 g. of 4-styrylpyridine, m.p. 131.5–133° C.

The latter (36.2, 0.2 mole), dissolved in 220 ml. of absolute ethanol and 30 ml. of concentrated hydrochloric acid, was reduced over 3.0 g. of platinum oxide under a hydrogen pressure of about 55 p.s.i. The product ws worked up in the manner described above in Preparation 1 and isolated in the form of the hydrochloride salt to give 43.5 g. of 4-(2-cyclohexylethyl)-piperidine hydrochloride, m.p. 246°–248° C.

Preparation 5

4-Phenylpyridine (15.5 g., 0.1 mole) dissolved in 185 ml. of absolute ethanol and 15 ml. of concentrated hydrochloric acid was reduced with hydrogen over 2 g. of platinum oxide under a hydrogen pressure of about 55 p.s.i. The product was worked up in the manner described above in Preparation 1 and isolated in the form of the hydrochloric salt to give 15.3 g. of 4-cyclohexylpiperidine hydrochloride. (The free base gives m.p. 106°–109° C.)

Preparation 6

To a mixture of 8.6 g. (0.36 mole) of magnesium turnings in 150 ml. of dry ether was added in small portions with cooling and stirring a solution of 45.0 g. (0.36 mole) of benzyl chloride in 75 ml. of anhydrous ether. When addition was complete, the mixture was stirred for about one hour and then treated dropwise with a solution of 26.6 g. of 4-chlorobutyronitrile in 95 ml. of ether. When addition was complete, the ether was gradually distilled off while replacing with an equal volume of toluene. The mixture was heated under reflux (at about 109° C.) for about 30 minutes, cooled to about 15° C., treated dropwise with 300 ml. of 10% aqueous ammonium chloride, filtered and the organic layer separated. The latter was washed with three 100 ml. portions of dilute hydrochloric acid, and the combined acid extracts were basified with solid potassium carbonate. Extraction of the mixture with ether and removal of the solvent from the combined organic extracts afforded an oil which was distilled in vacuo to give 13.05 g. of 2-benzyl-4,5-dihydropyrrole, b.p. 123°–125° C./13 mm., $n_D^{25}$ 1.5405.

The latter, dissolved in 210 ml. of ethanol and 15 ml. of concentrated hydrochloric acid was reduced with hydrogen over 2 g. of platinum oxide under a hydrogen pressure of about 50 p.s.i. The mixture was worked up in the manner described above in Preparation 1 and the product isolated in the form of the hydrochloride salt to give 16.8 g. of 2-cyclohexylmethylpyrrolidine hydrochloride, m.p. 130.5°–131.5° C. (from acetone).

Preparation 7

To a suspension of 11.2 g. (1.6 mole) of lithium wire in 600 ml. of anhydrous ether was added dropwise 125.6 g. (0.8 mole) of bromobenzene. When addition was complete, the mixture was stirred for about a half hour and then treated dropwise first with a solution of 74.4 g. (0.8 mole) of picoline in 100 ml. of anhydrous ether and then, after stirring for fifteen minutes, with a solution of 74.0 g. (0.4 mole) of 2-phenylethyl bromide in 100 ml. of ether. The mixture was stirred at ambient temperature for about twelve hours and then poured with stirring onto 300 g. of ice. When all excess lithium had reacted, the layers were separated, the aqueous layer washed with additional ether, and the combined organic portions were washed with brine, dried and taken to dryness to give a residual oil which was distilled in vacuo to give 41.3 g. of 2-(3-phenylpropyl)-pyridine, b.p. 76°–78° C./0.05 mm., $n_D^{25}$ 1.5592.

The latter (19.7 g., 0.1 mole) dissolved in 235 ml. of ethanol and 15 ml. of concentrated hydrochloric acid was reduced with hydrogen over 2 g. of platinum oxide under a hydrogen pressure of around 55 p.s.i. at about 65° C. The product was worked up in the manner described above in Preparation 1 and isolated in the form of the hydrochloride salt to give 22.2 g. of 2-(3-cyclohexylpropyl)piperidine hydrochloride, m.p. 175°–176.5° C. (from ethyl acetate).

Preparation 8

To a stirred suspension of 40.4 g. (0.3 mole) of aluminum chloride in 60 ml. of hexane was added 20 g. (0.15 mole) of isobutylbenzene. The mixture was stirred and cooled to about 5° C., and then treated dropwise over a two hour period with 15.2 g. (0.15 mole) of acetic anhydride. The mixture was stirred for an additional 3 hours, and then poured into a mixture of ice and 40 ml. of concentrated hydrochloric acid. The organic layer was separated, washed once with dilute potassium bicarbonate, once with saturated sodium chloride and then dried and evaporated to dryness to give 22.5 g. of 4-isobutylacetophenone.

A mixture of 0.91 mole of sodium isopropoxide was prepared by dissolving 21 g. of sodium metal in 700 ml. of isopropanol under a nitrogen atmosphere. The mixture was cooled to 14° C. and then treated dropwise over a period of 15 minutes with a mixture of 92 g. (0.52 mole) of 4-isobutylacetophenone and 120 g. (0.91 mole) of ethyl chloroacetate. The mixture was stirred for five hours at 8°–10° C., then for ten hours at ambient temperature, and finally refluxed for one hour. About 300 ml. of isopropanol was removed by distillation, and the mixture was diluted with 600 ml. of toluene and 600 ml. of water, shaken, and the aqueous layer removed and extracted with toluene. The combined toluene fractions were washed once with saturated sodium chloride and then dried and taken to dryness to give 164.7 g. of ethyl 3-methyl-3-(4-isobutylphenyl)glycidate as a dark brown liquid. The latter was refluxed for fifteen minutes in a solution of 15 g. of sodium hydroxide in 400 ml. of ethanol and 100 ml. of water. The mixture was then taken to dryness, and the residue [155.9 g. of crude sodium 3-methyl-3-(4-isobutylphenyl)glycidate] was steam distilled and the distillate extracted with ether. The extracts, on evaporation, afforded 83.5 g. of α-(4-isobutylphenyl)-propionaldehyde which was converted to the bisulfite complex (147.5 g.) by mixing with a saturated solution of sodium metabisulfite (360 g. in 580 ml. of water.)

About 30 g. of the bisulfite complex was cleaved with aqueous sodium carbonate and extracted into ether to give 14 g. of the corresponding aldehyde which was dissolved in 112 ml. of ethanol. The solution was treated with a solution of 30 g. of silver nitrate in 40 ml. of water, and a solution of 40 g. of potassium hydroxide in 50 ml. of wter was added dropwise over a thirty minute period. The mixture was heated under reflux for two hours, the ethanol removed by distillation, the mixture filtered, and the filtrate acidified with dilute hydrochloric acid. The greenish oil which separated was taken into ether, and the solution extracted with 10% potassium hydroxide. The alkaline solution was then acidified and extracted once again with ether to give 12 g. of material which was recrystallized from hexane to give 6.0 g. of α-(4-isobutylphenyl)propionic acid, m.p. 72°–73° C.

Preparation 9

Following a procedure similar to that described in Preparation 8 above, α-(3-bromophenyl)propionaldehyde (149.6 g.) was obtained from 314.8 g. of 3-bromoacetophenone and 363 g. of ethyl chloroacetate.

PREPARATION OF FINAL PRODUCTS

EXAMPLE 1

α-(4-Isobutylphenyl)propionaldehyde (8.6 g., 0.045 mole) and 8.4 g. (0.045 mole) of 2-cyclohexylmethylpiperidine were dissolved in 200 ml. of absolute ethanol in a Parr hydrogenator and the mixture reduced with hydrogen over 703 mg. of palladium-on-charcoal. Reduction was complete in about fifteen hours, and the mixture was filtered and the filtrate evaporated to dryness to give 16.3 g. of crude product which was chromatographed on 300 g. of alumina using 10% ether/90% hexane as eluent. There was thus obtained 10.0 g. of 2-cyclohexylmethyl-1-[2-(4-isobutylphenyl)propyl]piperidine as a colorless oil. The hydrochloride salt melts at 132°–160° C.

EXAMPLE 2

A mixture of 10.7 g. (0.056 mole) of α-(4-isopropylphenyl)propionaldehyde and 8.1 g. (0.056 mole) of 5-(N,N-diethyl)-2-pentylamine in ethanol was reduced with hydrogen over 700 mg. of palladium-on-charcoal in a Parr hydrogenator using the procedure described above in Example 1. The product was isolated in the form of the free base to give 10.0 g. of N-[2-(4-isobutylphenyl)propyl]-N-[5-(N',N'-diethylamino)-2-pentyl]amine as an oil.

EXAMPLE 3

A mixture of 36.0 g. (0.18 mole) of α-(4-isobutylphenyl)propionic acid and 34.7 g. (0.29 mole) of thionyl chloride in 61 ml. of benzene was refluxed for about three hours and then taken to dryness to give 38.1 g. of α-(4-isobutylphenyl)propionyl chloride as an orange oil.

The latter, dissolved in 70 ml. of ether, was added dropwise with stirring to a solution of 20.4 g. (0.18 mole) of 2,6-dimethylpiperidine and 23.7 g. (0.23 mole) of triethylamine in 70 ml. of anhydrous ether. The mixture was then filtered, and the filtrate washed twice with dilute hydrochloric acid, once each with aqueous bicarbonate and brine, and then dried and taken to dryness to give 43.3 g. of 2,6-dimethyl-1-[α-(4-isobutylphenyl)propionyl]piperidine, m.p. 60°–65° C. (from hexane).

A solution of the latter (42 g., 0.14 mole) dissolved in 200 ml. of ether was added dropwise with stirring at 15°–20° C. to a stirred suspension of 10.6 g. (0.28 mole) of lithium aluminum hydride in ether. When addition was complete, the mixture was stirred at ambient temperature for about 15 hours and then decomposed by the dropwise addition of 10.6 ml. of water. The mixture was then treated with 11 ml. of 15% sodium hydroxide, then an additional 30 ml. of water, diluted with ether, and filtered. The filtrate was washed with saturated sodium chloride, dried and evaporated to dryness to give 34 g. of 2,6-dimethyl-1-[2-(4-isobutylphenyl)propyl]piperidine as a yellow oil.

EXAMPLE 4

A solution of 256 g. (1.21 moles) of α-(3-bromophenyl)propionaldehyde and 432 g. (2.4 moles) of 2-cyclohexylmethylpiperidine in 6 liters of benzene was refluxed under a Dean-Stark trap for about fifteen hours. The solution was then taken to dryness to give 782.8 g. of a yellow oil. The latter was distilled in vacuo and the fraction boiling up to 100° C./1.0–0.6 mm. was collected and discarded. The undistilled residue of 414.6 g. was retained as 2-cyclohexylmethyl-1-[2-(3-bromophenyl)-1-propenyl]piperidine.

The latter (1.1 mole) was dissolved in 3 liters of hexane, and the solution was cooled in an ice bath and acidified by the addition of 235 ml. of 6.1N ethereal hydrogen chloride. The material which separated was collected, washed with ether, and dissolved in 3.5 liters of dimethylformamide. The solution was treated portionwise with 80 g. (2.1 moles) of sodium borohydride and the mixture was then stirred at room temperature for about one and a half hours. The mixture was then basified with one liter of 10% sodium hydroxide and extracted with hexane. The combined hexane washes, on drying and evaporation to dryness, afforded 442.6 g. of a yellow oil which was distilled in vacuo to give 344.4 g. of 2-cyclohexylmethyl-1-[2-(3-bromophenyl)propyl]piperidine, b.p. 156°–170° C./0.5 mm.

EXAMPLE 5

A solution of 68 g. (0.18 mole) of 2-cyclohexylmethyl-1-[2-(3-bromophenyl)propyl]piperidine in 150 ml. of ether was stirred and cooled to 10° C. and then treated with 0.32 mole of N-butyl lithium in diethyl ether. The solution was stirred for about a half hour at about 10° C., then for an hour at ambient temperature and finally at reflux for a half hour. The mixture was then cooled in an ice bath, treated with 200 ml. of 10% sodium hydroxide, stirred for ten minutes, filtered, and the organic layer separated, washed with brine, dried and evaporated to dryness to give 98 g. of residue. The latter was dissolved in a solution containing 1.5% isopropylamine in hexane and chromatographed on 1500 g. of alumina. The most rapidly moving band was removed and, on evaporation of solvent, gave 9.7 g. of material which was distilled in vacuo. There was thus obtained 7.4 g. of 2-cyclohexylmethyl-1-(2-phenylpropyl)piperidine, b.p. 167°–173° C./0.07 mm.

Using the procedure described above in Example 4, the same compound was obtained in 69% overall yield from 40.2 g. (0.3 mole) of α-phenylpropionaldehyde and 109 g. (0.6 mole) of 2-cyclohexylmethylpiperidine in 1250 ml. of benzene and reduction of the resulting 74.5 g. of 2-cyclohexylmethyl-1-[2-phenyl-1-propenyl]piperidine with 14 g. (0.37 mole) of sodium borohydride in 280 ml. of hexane and 400 ml. of dimethylformamide after reaction of the amine with 55 ml. of 6.1N ethereal hydrogen chloride.

EXAMPLE 6

Following a procedure similar to that described in Example 4, 10.65 g. (0.05 mole) of α-(3-bromophenyl)propionaldehyde was reacted with 16.73 g. (0.1 mole) of 2-cyclohexylmethylpyrrolidine in 250 ml. of benzene using a Dean-Stark trap, and the resulting 2-cyclohexylmethyl-1-[2-(3-bromophenyl-1-propenyl]pyrrolidine converted to the corresponding iminium chloride and reduced with sodium borohydride in dimethylformamide to give 4.9 g. of 2-cyclohexylmethyl-1-[2-(3-bromophenyl)propyl]pyrrolidine hydrochloride, m.p. 150°–154° C. (from acetone/ether).

Following a procedure similar to that described in Example 3, the following compounds of formula I are similarly prepared.

EXAMPLE 7

2-Cyclohexyl-1-[2-(4-vinylphenyl)ethyl]piperidine prepared by reaction of 4-vinylphenylacetyl chloride [from 4-vinylphenylacetic acid-Bergman, J. Org. Chem. 24, 549–51 (1959)] with 2-cyclohexylpiperidine followed by lithium aluminum hydride reduction of the resulting 2-cyclohexyl-1-[(4-vinylphenyl)acetyl]piperidine.

EXAMPLE 8

2-(2-Cyclohexylethyl)-1-[2-(4-chlorophenyl)ethyl]piperidine prepared by reaction of 4-chlorophenylacetyl chloride with 2-(2-cyclohexylethyl)piperidine followed by reduction with lithium aluminum hydride of the resulting 2-(2-cyclohexylethyl)-1-[(4-chlorophenyl)acetyl]piperidine.

EXAMPLE 9

4-(2-Cyclohexylethyl)-1-[2-(3-ethylphenyl)ethyl]piperidine prepared by reaction of 3-ethylphenylacetyl chloride with 4-(2-cyclohexylethyl)piperidine followed by reduction with lithium aluminum hydride of the resulting 4-(2-cyclohexylethyl)-1-[(3-ethylphenyl)acetyl]piperidine.

EXAMPLE 10

4-Cyclohexyl-1-[2-methylphenyl)ethyl]piperidine prepared by reaction of 2-methylphenylacetyl chloride with 4-cyclohexylpiperidine followed by reduction with lithium aluminum hydride of the resulting 4-cyclohexyl-1-[(2-methylphenyl)acetyl]piperidine.

EXAMPLE 11

2-(3-Cyclohexylpropyl)-1-[2-(4-sec.-butylphenyl)ethyl]piperidine prepared by reaction of 4-sec.-butylphenylacetyl chloride with 2-(3-cyclohexylpropyl)piperidine followed by reduction with lithium aluminum hydride of the resulting 2-(3-cyclohexylpropyl)-1-[(4-sec.-butylphenyl)acetyl]piperidine.

EXAMPLE 12

2-Methyl-1-(2-phenylpropyl)hexamethyleneimine prepared by reaction of α-phenylpropionyl chloride with 2-methylhexamethyleneimine [Mueller et al., Monatsh 61, 212–218 (1932)] followed by reduction with lithium aluminum hydride of the resulting 2-methyl-1-(α-phenylpropionyl)hexamethyleneimine.

EXAMPLE 13

Following a procedure similar to that described in Example 4, 21.3 g. (0.1 mole) of α-(3-bromophenyl)-propionaldehyde was reacted with 39.0 g. (0.2 mole) of 2-(2-cyclohexylethyl)piperidine in 250 ml. of benzene using a Dean-Stark trap, and the resulting 2-(2-cyclohexylethyl)-1-[2-(3-bromophenyl)-1-propenyl]-piperidine converted to the corresponding iminium chloride and reduced with 6 g. (0.16 mole) of sodium borohydride in 250 ml. of dimethylformamide to give 37.3 g. of 2-(2-cyclohexylethyl)-1-[2-(3-bromophenyl)propyl]piperidine as a clear viscous oil.

Anal. Calcd. for $C_{22}H_{34}BrN$: C,67.33; H,8.73; N,3.57. Found: C,67.51; H,8.67; N,3.62.

EXAMPLE 14

Following a procedure similar to that described in Example 4, 21.3 g. (0.1 mole) of α-(3-bromophenyl)-propionaldehyde was reacted with 38.5 g. (0.18 mole) of 2-(3-cyclohexylpropyl)piperidine in 250 ml. of benzene using a Dean-Stark trap, and the resulting 2-(3-cyclohexylpropyl)-1-[2-(3-bromophenyl)-1-propenyl]-piperidine converted to the corresponding iminium chloride and reduced with 6.5 g. (0.17 mole) of sodium borohydride in 225 ml. of dimethylformamide to give 21.8 g. of 2-(3-cyclohexylpropyl)-1-[2-(3-bromophenyl)propyl]piperidine as a viscous oil.

Anal. Calcd. for $C_{23}H_{36}BrN$: C,67.97; H,8.93; N,3.45. Found: C,67.65; H,9.01; N,3.39.

The phenyl-lower-alkylamines of formula I of the invention have been tested in the carrageenin edema (CE) and adjuvant arthritis (AA) tests and found to have anti-inflammatory activity. Data so-obtained, stated in terms of percent inhibition at a dose expressed in terms of millimoles ($\mu$M)/kg., are given below. All data were obtained on oral administration.

| Example | CE (% Inhib./$\mu$M/kg.) | AA (% Inhib./$\mu$M/kg.) |
|---|---|---|
| 1 | 0%/0.08 | 75%/0.324 |
|   | 5%/0.324 |  |
| 2 | 0%/0.02 | 32%/0.01 |
|   | 17%/0.08 | 34%/0.04 |
|   | 39%/0.324 | 63%/0.16 |
| 3 | 0%/0.08 | 55%/0.324 |
|   | 8%/0.324 |  |
| 4 | 7%/0.005 |  |
|   | 4%/0.02 |  |
|   | 0%/0.08 |  |
| 5 | 0%/0.005 |  |
|   | 16%/0.02 |  |
|   | 13%/0.08 |  |

I claim:

1. A compound having the formula:

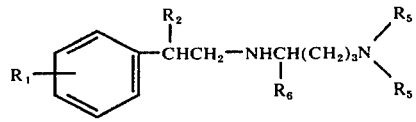

where $R_1$ represents lower-alkyl containing from one to four carbon atoms; $R_2$ represents methyl; $R_5$ represents ethyl; and $R_6$ represents methyl.

2. N-[2-(4-Isobutylphenyl)propyl]-N-[5-(N',N'-diethylamino)-2-pentyl]amine according to claim 1.

* * * * *